United States Patent [19]

Tanaka et al.

[11] 3,985,779

[45] Oct. 12, 1976

[54] M-PHENOXYPHENYL PROPIONIC ACID DERIVATIVES AND PREPARATION THEREOF

[75] Inventors: Satoru Tanaka; Kazunori Hashimoto, both of Higashi-Kurume; Hideaki Watanabe, Ushiku; Keiichi Munakata, Ohmiya, all of Japan

[73] Assignee: Eisai Co., Ltd., Tokyo, Japan

[22] Filed: Oct. 29, 1974

[21] Appl. No.: 518,935

[30] Foreign Application Priority Data

| Oct. 29, 1973 | Japan | 48-120738 |
| Oct. 29, 1973 | Japan | 48-120739 |
| May 16, 1974 | Japan | 49-53897 |

[52] U.S. Cl. .................... 260/448 R; 260/520 R; 424/317
[51] Int. Cl.$^2$ .................................... C07F 5/06
[58] Field of Search ................ 260/448 R, 520 R; 424/317

[56] References Cited

UNITED STATES PATENTS

| 3,385,886 | 5/1968 | Nicholson et al. | 260/520 R X |
| 3,517,051 | 6/1970 | Bolhofer | 260/448 R X |
| 3,600,437 | 8/1971 | Marshall | 260/448 R X |
| 3,649,679 | 3/1972 | Marshall | 260/520 R |
| 3,766,263 | 10/1973 | Godfrey | 260/520 R |

Primary Examiner—Helen M. S. Sneed
Attorney, Agent, or Firm—Wenderoth, Lind & Ponack

[57] ABSTRACT

New meta-phenoxyphenyl propionic acid derivatives and pharmacologically acceptable salts thereof having excellent anti-inflammatory and analgesic activities with low toxicity are provided. The new compounds are adapted for therapeutical treatment of various inflammatory diseases by oral administration without injurious by-effects; successive administrations for an elongated period are not accompanied with an appreciable gastric irritability and the like.

9 Claims, No Drawings

M-PHENOXYPHENYL PROPIONIC ACID DERIVATIVES AND PREPARATION THEREOF

This invention relates to the new m-phenoxypropionic acid derivatives or more particularly 2-(m-phenoxyphenyl)propionic acid derivatives represented by the chemical formula (I):

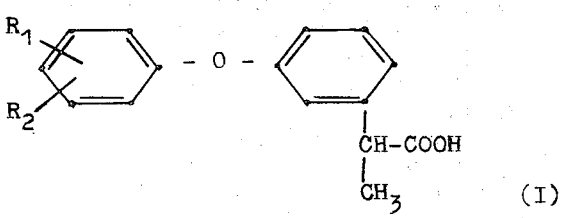

(I)

wherein $R_1$ and $R_2$ are hydrogen or halogen atoms or trifluoromethyl, lower alkyl or lower alkoxy groups with the proviso that there is no case where the both $R_1$ and $R_2$ simultaneously are hydrogen atoms, and preparation thereof.

The new compounds of the formula (I) according to the present invention possess excellent anti-inflammatory and analgesic activities and are therefore useful as non-steroidal anti-inflammatory and analgic agents suitable for the treatment of diseases such as, articular rheumatism, arthritis, spondylitis, tendinitis, fracture, distorsion, postoperative inflammation, olitis media, nasosinusitis, neuralgia, lumbago, rachialgia, odontalgia and the like.

Other than non-steroidal analgic and anti-inflammatory agents such as indole-, pyrazole-, and anthranilic series compounds, pharmacological investigations have recently been effected with regard to phenyl propionic acid and phenylacetic acid derivatives.

Actually, Ibuprofen preparation consisting of 2,4'-isobutylphenyl propionic acid, for example, is available in market and used broadly for the purpose of therapeutic treatments.

As non-steroidal analgic and anti-inflammatory agents, the compounds of indole and pyrazole series have hitherto been broadly employed. However, since administration of these known compounds is accompanied with injurious by-effects such as gastrointestinal impediment exciting nausea, aggravation of ulcers and the like; headache, dizziness and the like, they are not adapted for consecutive medications during an elongated period.

Our study has been directed to the development of an anti-inflammatory medicament of mild activity and thus capable of consecutive administrations for an elongated period without injurious by-effects, and thus adaptable for medication to a patient that does not particularly endure administration of a severe anti-inflammatory agent or a patient of chronic inflammation who requires consecutive administrations for an elongated period.

For the establishment of the abovementioned desires, the present inventors had devoted ourselves to investigate on several derivatives of phenyl alkanic acid. As the result of the investigations, it has been found that 2-(m-phenoxyphenyl)propionic acid derivatives represented by the chemical formula:

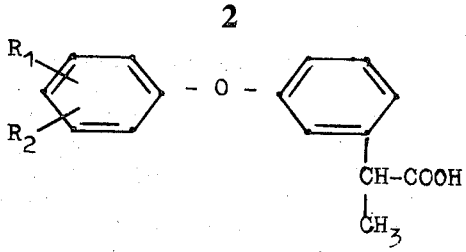

wherein $R_1$ and $R_2$ are hydrogen or halogen atoms or trifluoromethyl, lower alkyl, or lower alkoxy groups with the proviso that there is no case where both $R_1$ and $R_2$ are simultaneously hydrogen atoms, are superior to the hitherto known anti-inflammatory agent belonging to phenylpropionic acid series with respect to anti-inflammatory activity, low-toxicity and tolerancy, and is thus an useful anti-inflammatory agent capable of consecutive administrations for an elongated period of time.

Accordingly, one of the objects of the present invention is to provide a new analgic and anti-inflammatory medicament.

Another object of this invention is to provide a new anti-inflammatory medicament without injurious by-effects which is adaptable to administrate consecutively for an elongated period.

Further object of this invention is to provide several methods preferable for producing said new anti-inflammatory agent.

Still further object of this invention is to provide therapeutic composition which contains said new compound as the active ingredient therefor in order to relieve of inflammation as well as pain, swelling, fever and the like in man, accompanying therewith.

Additional object of this invention is to provide method for treating the aforementioned inflammations in man.

The new 2-(m-phenoxyphenyl)propionic acid derivatives of the present invention may be prepared by several methods including the following five alternative methods A), B), C), D) and E):

Method A

This method is illustrated by the step of the following schematical equation:

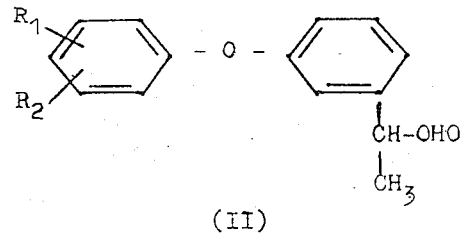

(II)

Oxidation ⟶

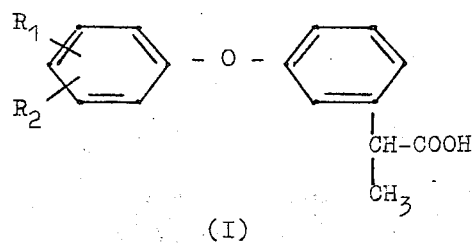

(I)

wherein $R_1$ and $R_2$ have the meanings same as those aforementioned.

In carrying out the method, 2-(m-phenoxyphenyl)-propionaldehyde derivatives of the formula (II) is subjected to reaction with an oxidizing agent to obtain 2-(m-phenoxyphenyl)propionic acid derivatives of the formula (I) as the contemplated substance.

As to the oxidizing agent to be employed, there may be mentioned those which are capable of converting usual aldehyde group into the corresponding carboxylic group, such as potassium permanganate, chromic acid anhydride, silver oxide, lead oxide, hydrogen peroxide and the like.

It has been found that a good result is obtained when the process is conducted in a mixture of water and alcohol; water or acetone as the reaction medium.

The compound of the formula (II) employed as the starting material for carrying out the abovementioned method A) is also a new compound which may be synthetically prepared in accordance with the following schematical equations:

wherein $R_1$ and $R_2$ have the meanings same as those aforementioned.

In practice of the abovementioned chemical reaction, the ketonic compound of the formula (III) is subjected to reaction in the presence of sodium ethylate with ethyl ester of chloroacetic acid to result in a corresponding ethylene oxide of the formula (IV), which is then subjected to hydrolytic decomposition to a corresponding free acid of the formula (V). The latter compound is finally decarbonized to the purposed compound of the formula (II). The reaction system is generally known as Darzens' reaction. [See G. Darzens, Compt. Rend. 139, 1214 (1904).]

The compound of the formula (II) is a viscous oily substance, which when derived from the compound of the formula (III), may immediately be employed without purification as the starting material for carrying out the aforementioned Method A).

Method B

This method is illustrated by the steps of the follow-

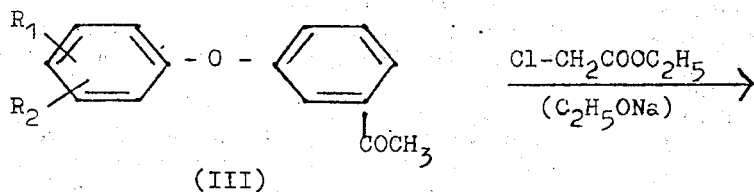

(III)

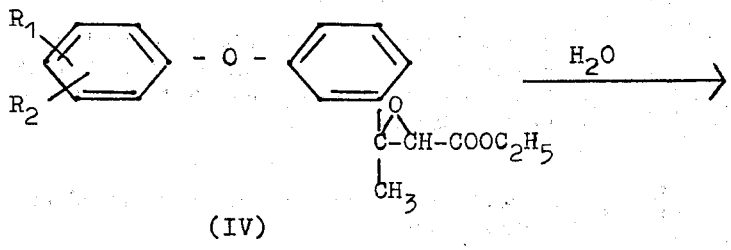

(IV)

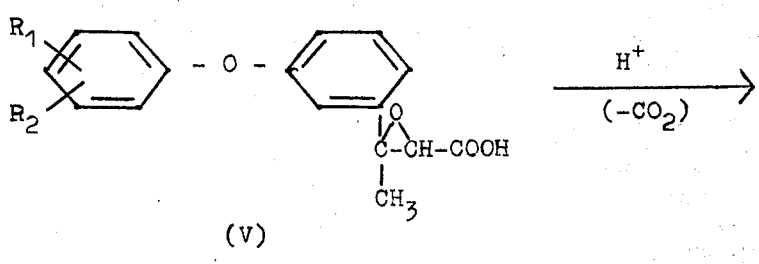

(V)

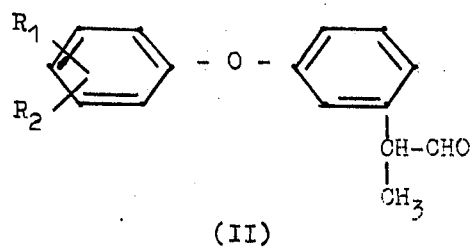

(II)

ing schematical equations:

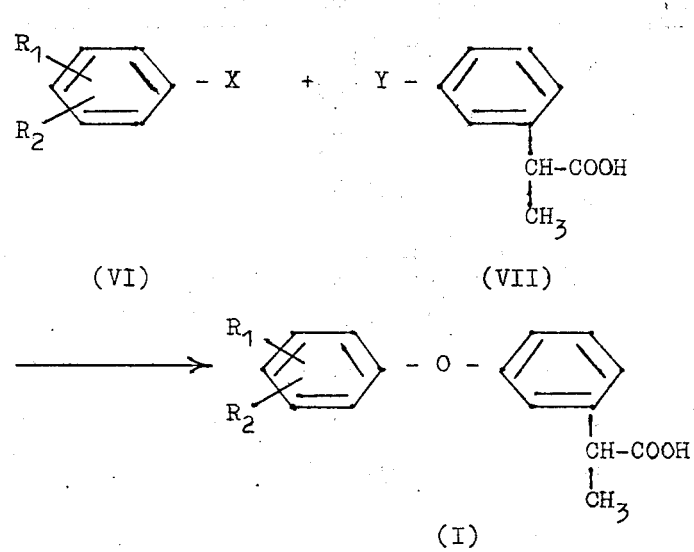

wherein $R_1$ and $R_2$ have the same meanings as those aforementioned; X and Y are halogen atoms or hydroxyl groups or alkali metal salts thereof with the proviso that when X is a halogen atom, Y is hydroxy group or its alkali metal salt, whereas when Y is halogen atom, X is hydroxyl group or its alkali metal salt.

In practice, where the process is carried out starting from the halide compound (VI′) as an embodiment of the compound of the formula (VI), the same is subjected to reaction with 2-(m-hydroxyphenyl)propionic acid or its alkali metal phenolate (VII′) as an embodiment of the compound of the formula (VII); whereas when the process is carried out starting from a phenol compound or a corresponding alkali metal phenolate (VI″) as an embodiment of the compound of the formula (VII), the same is subjected to reaction with 2-(m-halogeno-phenyl)propionic acid (VII′) as an embodiment of the compound of the formula (VII). The contemplated compound of the formula (I) is thus obtained equally by these processes. The reaction is preferably effected in an alkaline condition in the absence or presence of a reaction medium, such as an alcoholic solution of caustic alkali, dimethyl formamide, dimethylsulfoxide and the like. The reaction is conducted smoothly by the addition of a catalyst such as pulverized metallic copper or halide of copper to the reaction system.

The compound of the formula which is employed as the starting material for carrying out the process of the present invention is also a new compound and may synthetically be prepared in accordance with the following processes A) and B):

Process A):

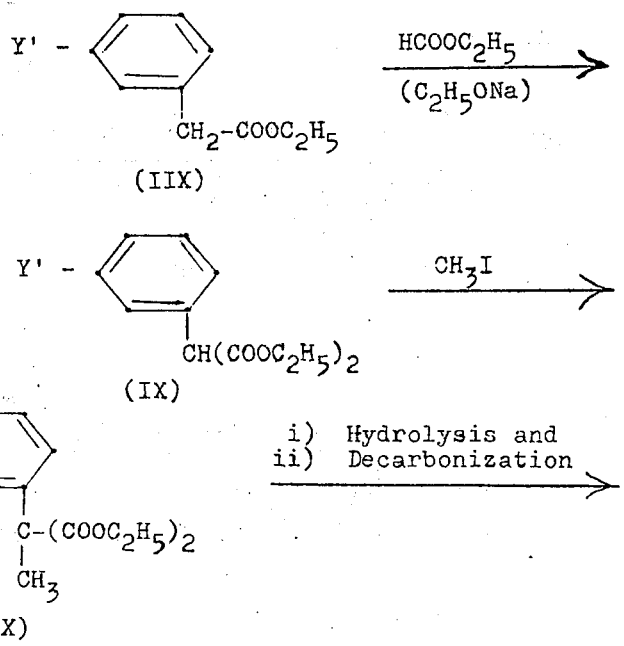

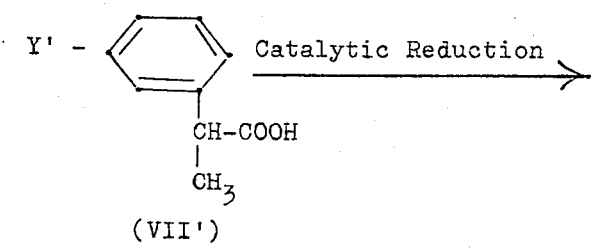

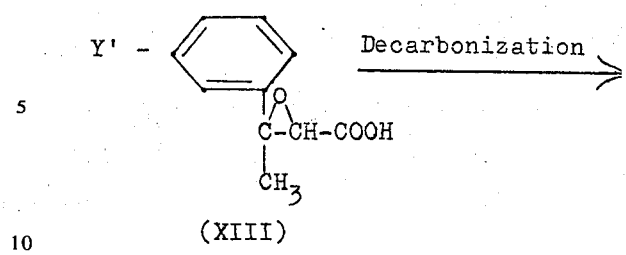

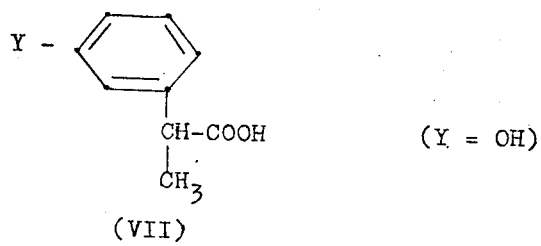

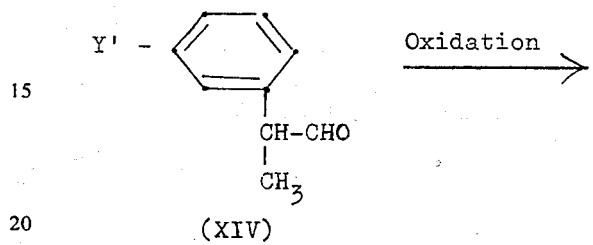

In the above formulae, Y' is halogen atom or a protected hydroxyl group.

Carbonic acid ethyl ester is first subjected to reaction in the presence of sodium ethylate with m-substituted phenylacetic acid ethyl ester of the formula (IIX) to form the corresponding malonic acid ethyl ester compound of the formula (IX). The compound of the formula (X) obtained by the reaction of methyl iodide on said ethyl ester (IX) is hydrolized and decarbonized to form the compound of the formula (VII'). In the compound (VII') where Y' is a halogen atom, then said compound is a type of the starting material (VII). When a compound on the other hand, is wanted in which Y is hydroxyl group, the same may be obtained by catalytic reduction of a compound of the formula (VII') which contains Y' being the hydroxyl group protected with methyl, benzyl or the like group followed by splitting off of said protected group.

Process B)

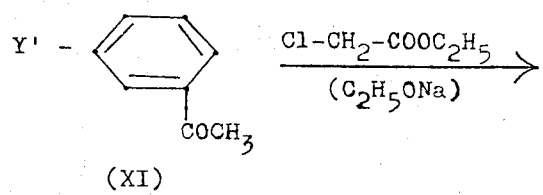

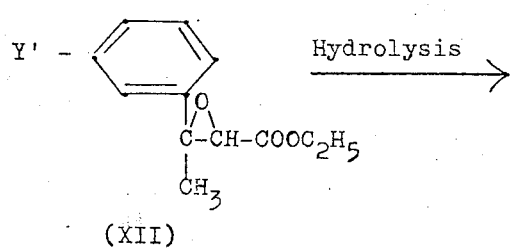

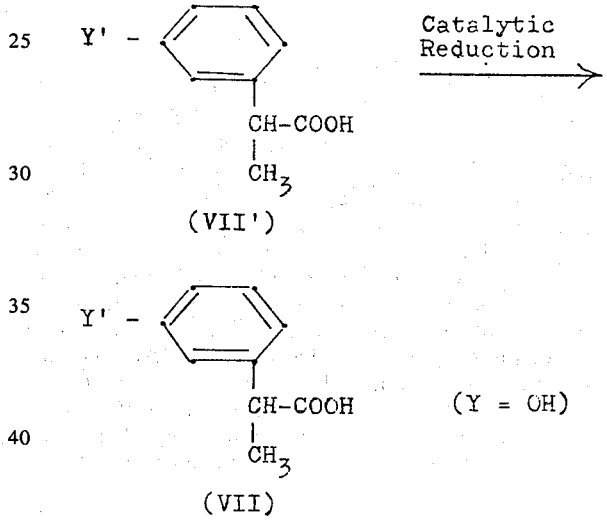

In practice, m-substituted acetophenone of the formula (XI) is subjected to reaction in the presence of sodium ethylate with chloroacetic acid ethyl ester to form 3-(m-substituted-phenyl)-2,3-epoxy-butylic acid ethyl ester of the formula (XII). The latter compound is hydrolyzed to the corresponding free acid of the formula (XIV), which is then decarbonized to 2-(m-substituted-phenyl)propionaldehyde of the formula (XIV), which is then oxidized to the compound of the formula (VII'). This compound (VII'), when Y' is a halogen atom, is a type of the starting material of the formula (VII), whereas a compound is wanted in which Y is hydroxyl group, the same can be obtained by catalytic reduction of a compound of the formula (VII') which contains Y' being the hydroxyl group protected with methyl, benzyl or the like group followed by splitting off of said protected group.

The compound of the formula (VII) wherein Y is hydroxyl group may readily be converted into the corresponding alkali metal phenolate by treating it with an alcoholic solution of alkali metal hydroxide.

Method C

This method is illustrated by the steps of the following schematical equations:

Step 1

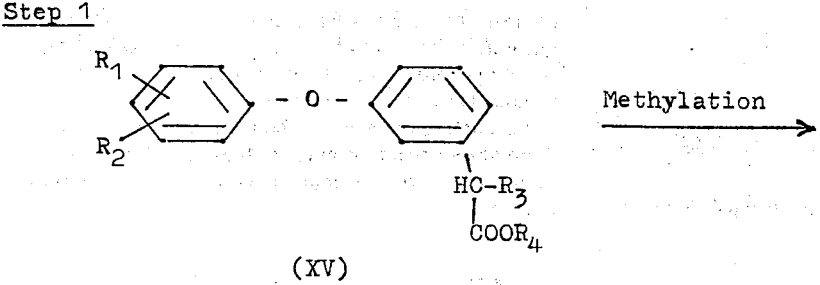

(XV)

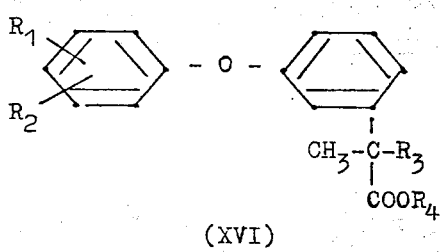

(XVI)

Step 2

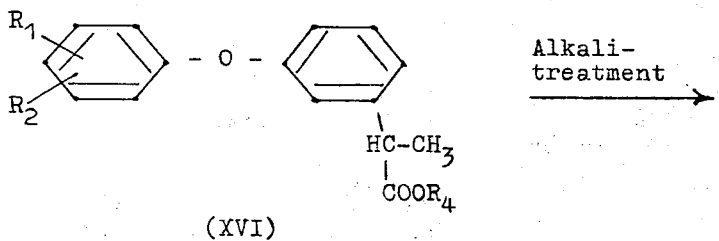

(XVI)

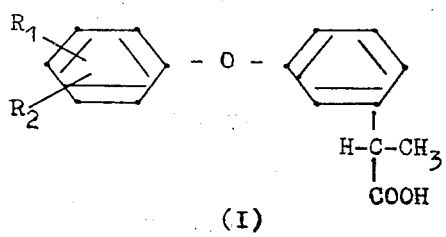

(I)

In the above formulae, $R_1$ and $R_2$ have the meanings same as those aforementioned; $R_3$ is CN or $COOR_5$; and $R_4$ and $R_5$ are hydrogen atoms or lower alkyl groups.

In carrying out the method, m-phenoxyphenyl acetic acid derivatives represented by the above formula (XV) is subjected to reaction in accordance with Step 1 with methylating agent such as methyl iodide, dimethyl sulfate and the like to form m-phenoxyphenyl propionic acid compound of the above formula (XVI); and in Step 2, the compound of the formula (XVI) thus obtained is treated with an alkaline agent such as alkali carbonate, caustic alkali and the like to cause hydrolysis and decarbonization of said compound to result in the purposed compound of the formula (I).

It is desirable to carry out smoothly the methylation of Step 1 by adding an alkaline agent such as sodium alcolate in lower alcohol to the reaction system, whereby the alcohol serves as a reaction medium. On the other hand, it is desirable to carry out Step 2 by employing an caustic alkali such as caustic soda, caustic potash and the like. Steps 1 and 2 can advantageously be conducted in a continuous manner without isolation of the intermediate product of the formula (XVI).

The compound of the formula (XVII) used as the starting material in carrying out the method C) is a new substance which may be prepared as follows:

a. The compound in which $R_3$ in said formula (XV) is CN may be obtained by causing a carbonic acid-lower alkyl ester or chlorocarbonic acid-lower alkyl ester to reaction with 3-(o-phenoxy)phenyl acetonitrile represented by the formula;

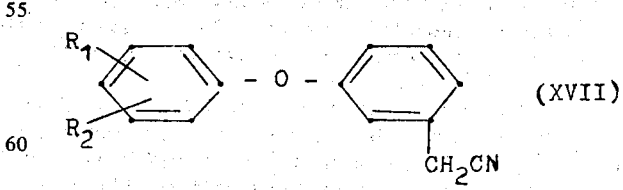 (XVII)

wherein $R_1$ and $R_2$ have the meanings same as those aforementioned.

b. The compound in which $R_3$ in said formula (XV) is $COOR_5$ may be obtained by causing a carbonic acid-lower alkyl ester or chlorocarbonic acid-lower alkyl ester to reaction with 3-(o-phenyl)phenoxy acetic acid compound represented by the formula:

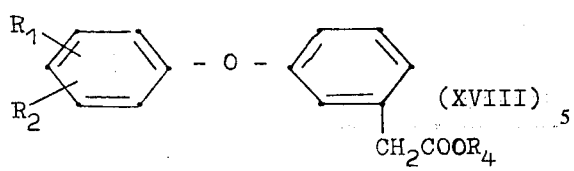

(XVIII)

wherein $R_1$, $R_2$ and $R_4$ have the meanings same as aforementioned.

Method D.

This method is illustrated by the steps of the following schematical equations:

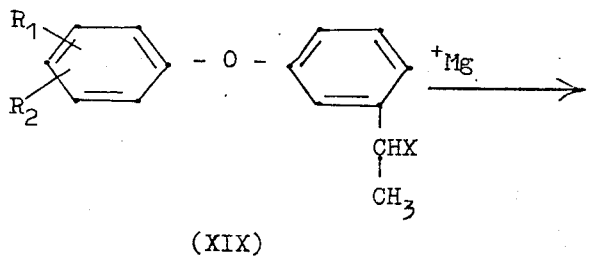

(XIX)

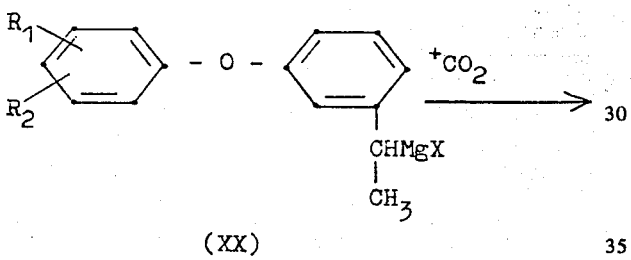

(XX)

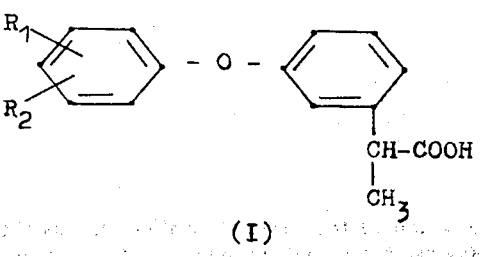

(I)

wherein $R_1$ and $R_2$ have the meanings same as those aforementioned, and X is halogen atom such as Cl, Br or I.

In carrying out the method, phenethyl halide derivative of the formula (XIX) is subjected to reaction with metallic magnesium to obtain phenethyl magnesium halide derivative of the formula (XX). The latter compound is subjected to reaction with carbon dioxide to produce the intended compound of the formula (I). The reactions taking place are generally known as "Grignard's reaction".

The steps of the reaction are preferably conducted in an inert solvent such as dry ether, tetrahydrofuran, isopropyl ether, benzene and dimethyl cellosolve and under inert gaseous atmosphere such as gaseous nitrogen, argon and the like.

When most of the metallic magnesium disappeared by dissolution, which is sign of the completion of the reaction, the reaction mixture is poured in an inert solvent such as ether or benzene which contains an excess amount of pulverized solid carbon dioxide. The reaction mixture is stirred as such, and from the reaction liquor from which the excess solid carbon dioxide has evaporated up, the purposed compound of the formula (I) can be recovered.

The starting material of the formula (XIX) employed in the above reaction may synthetically be prepared in accordance with the steps of the following schematical equations:

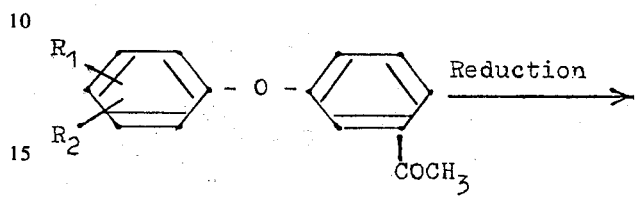

(XXI)

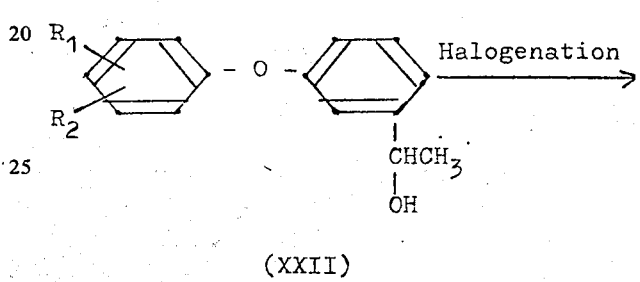

(XXII)

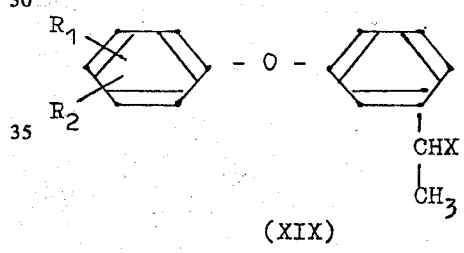

(XIX)

Method E

This method is illustrated by the step of the following schematic equation:

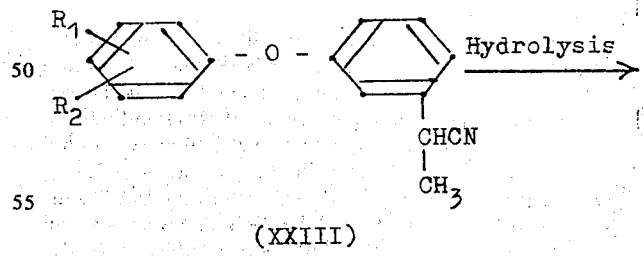

(XXIII)

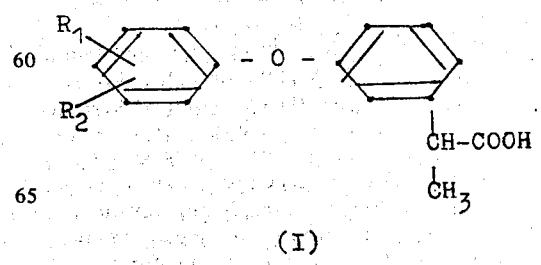

(I)

wherein $R_1$ and $R_2$ have the meanings same as those aforementioned.

In carrying out this method, the propionitrile derivative of the formula (XXIII) is subjected to hydrolysis to obtain the intended compound of the formula (I).

The hydrolysis may be effected by the use of an acid such as sulfuric, hydrochloric and acetic acids or an alkaline substance such as caustic alkali and alkali carbonate. The corresponding acid amide may occasionally be separated out as an intermediate from the reaction system. The intended reaction may, however, be performed, if such a reaction system as such is further subjected to reaction.

The starting material of the formula (XXIII) employed in the above reaction may synthetically be prepared in accordance with the steps of the following schematic equations:

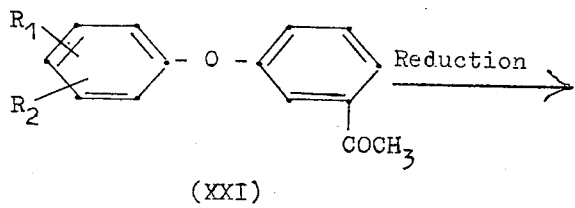

(XXI)

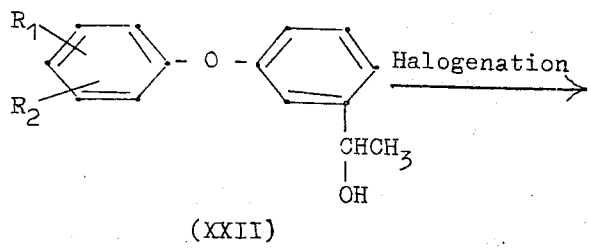

(XXII)

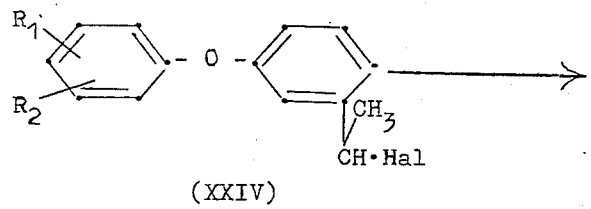

(XXIV)

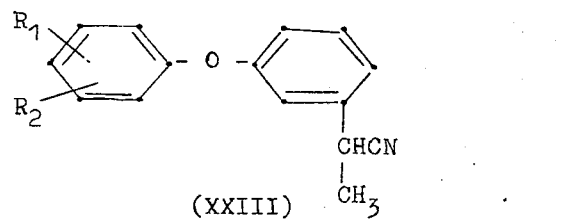

(XXIII)

wherein $R_1$ and $R_2$ have the meanings same as those aforementioned.

In carrying out the reaction steps, the phenethyl alcohol derivative of the formula (XXII) is first formed by reduction on acetophenone of the formula (XXI). The reaction product is halogenized by treating it with a halogenating agent such as phosphor pentachloride, thionyl chloride, phosphor tribromide, hydrobromic acid and the like to obtain the corresponding halo-derivative of the formula (XXIV). The latter compound is heated in a solvent with cyanide compound such as sodium and potassium cyanides to result in the intended compound of the formula (XXIII).

The compound of the formula (I) prepared by the abovementioned several methods may be converted into its pharmacologically acceptable metal salts.

As for the pharmacologically acceptable metal salts, there may be mentioned salts of sodium, potassium, magnesium, calcium, aluminium and the like. Among others, aluminium salt is especially adapted for obtaining pharmacological product with low gastrointestinal impediment.

The pharmacological effects exhibited by m-phenoxyphenyl propionic acid derivatives of the present invention are shown by the following several Experiments.

m-Phenoxyphenyl propionic acid derivatives represented by the hereinunder-mentioned general formula, which are employed in the Experiments, are listed in the following Table 1 together with the known compounds (1) and (2) for the sake of comparison.

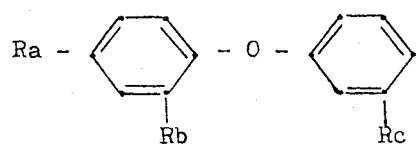

| Sample | Ra | Ab | Rc | Aluminium salt |
|---|---|---|---|---|
| (1) | H | H | $CH(CH_3)COOH$ | — |
| (2) | H | H | $CH(CH_3)COO-$ | $[CH(CH_3)COO]_2 \cdot Al(OH) \cdot 2H_2O$ |
| (3) | Cl | H | $CH(CH_3)COOH$ | — |
| (4) | Cl | H | $CH(CH_3)COO-$ | $[CH(CH_3)COO]_2 \cdot Al(OH) \cdot 2H_2O$ |
| (5) | H | Cl | $CH(CH_3)COOH$ | — |
| (6) | $CF_3$ | H | $CH(CH_3)COOH$ | — |
| (7) | F | H | $CH(CH_3)COO-$ | $[CH(CH_3)COO]_2 \cdot Al(OH) \cdot 2H_2O$ |

In Table 1, samples (1) known as trade name "Fenoprofen" as shown in Fed. Proc. Vol. 30, 563 (1971), for example, possess anti-inflammation activity, too.

In addition to the above experiments, the anti-inflammatory activity of the compounds of the invention was compared with that of Ibuprofen, (2,4′-isobutylphenyl-propionic acid), which has broadly been employed as anti-inflammatory agent of the phenylpropionic acid compounds.

Experiment A.

Inhibitory activity on Carrageenin-induced Edema in rats

Carrageenin was used as the agent for inducing edema and 5 male rats of Wistar strain having body weight of about 150 grs. after fasting for 16–17 hours were used as test animals. The inhibitory activity of the test compounds were determined with the paw edema method in accordance with Winter C. A. et al; Proc. Soc. Exp. Biol. Med. 111, 544 (1962).

The compounds were suspended in an aqueous solution of gum arabic and the same were orally administered to the rats at 1 hour before the injection of Carrageenin.

The observation was effected by measuring, after 3 hours the administration of the Carrageenin, the enlarged volumes of hind paw of the rats. The results are shown in Table 2 later given.

As is evident from the data in Table 2, it is noted that the compounds of the present invention show 40 – 50 % of inhibition of the edema, when 40 – 50 mg/kg of the compounds were orally administered to the rats.

Experiment B.

Inhibitory activity on Kaolin-induced Edema in Rats

Kaolin was used as the agent for inducing edema, and the inhibitory effect on edema was observed in accordance with the procedure disclosed in preceding Experiment (A). The results of the observation are shown in Table 3 later given.

As is evident from the data in Table 3, it is noted that the compounds of the present invention show 40 – 50 % inhibitory effect on edema when 40 – 50 mg/kg of the compounds were orally administered to the rats, whereas Ibuprofen as the comparison shows only 15% edema-inhibitory activity in oral administration in the same dosage as the above.

Experiment C.

Inhibitory activity on dextran-induced edema in rats

Experiment was carried out in the manner same as those of the preceding Experiments in which dextran was employed as irritant substance. The results thus observed are shown in Table 4 later given.

Experiment D.

Inhibitory activity on anti-rat-rabbit serum (ARRS)-induced edema in rats

Similar Experiments was carried out by using ARRS as irritant substance. The results observed are shown in Table 5 later given.

Experiment E.

Inhibitory activity on Adjuvant arthritis in rats

After lapse of 14 days from the injection of Adjuvant, including mycobacterium tuberculosis 40 mg/kg of Ibuprofen and the abovementioned compound (5) in Table 1 were successively orally administered for 9 days. The inflammatory score and the volumes of the right and left paws of the rats were observed.

The results of the observation are shown in Table 6 later given.

From the data in Table 6, it is noted that a significant inhibitory activity in score and paw volume are presented with the compound (5).

Experiment F.

Inhibitory activity on granuloma induced by Formalin Filter paper Pellet in rats The results of the observation are shown in Table 7 later given.

As shown in Table 7, it is noted that the inhibitory activity on granuloma was shown by oral administrations of 8 and 40 mg/kg/day for successive 6 days. The compound (5) of the invention gave a significant effect as compared with the control. Ibuprofen, on the contrary, was entirely not effective.

Experiment G.

Observation of gastric irritability

Gastric irritability due to oral administration of the compounds as edema inhibitory agent was studied by macroscopical observation of the dissected stomachs of the rats which had been employed for determination of the edema inhibitions mentioned in the preceding paragraphs. The degrees of the irritability observed were scored in the 0 to 10 ratings depending upon the extent of errosions and bleedings of the stomachs, wherein the rating of 0(zero) means "nothing unusual", the rating of 10 means a state of considerable gastric irritability with bleeding and the remainders mean the intermediate degree of gastric irritability.

The results are shown in Table 8.

Table 8

| Compounds | Dosage (mg/kg) | Degree of gastric irritability |
|---|---|---|
| Aspirin | 100 | 10 |
| Compound (1) | 50 | 3 |
| Compound (2) | 50 | 3 |
| Compound (5) | 50 | 2 |

From the abovementioned Experiments A – G, it has been found the followings:

i. The compounds of the present invention show an excellent inhibitory activity on edema induced with the various inflammatory agents which is comparable to or over those induced with the known Fenoprofen and Ibuprofen. It is pratically notable that the compound (5), i.e., 2-[m-(o-chlorophenoxy)phenyl]propionic acid of the present invention is most effective as the anti-inflammatory agent.

In the Experiment with known Ibuprofen, the compounds of the present invention clearly exhibit the significant and superior inhibitory activity to Adjuvant arthritis and the granuloma proliferation.

ii. In the abovementioned Experiments, it has not been observed an appreciable gastric irritability due to the oral administration of the compounds of the present invention to the rats.

Experiment H.

Comparison of toxicity of the phenyl propionic acid derivatives of the present invention and that of the other known anti-inflammatory agents was carried out in mice. The result obtained are listed in Table 9 which is given later.

As is evident from the data given in Table 9, the acute toxicity due to the phenoxyphenyl propionic acid derivatives of the invention is almost equivalent to that due to Ibuprofen.

It is thus apparent that the security in dosage of the compounds of the present invention is higher than those of Indomethacin, Phenyl-butazone and the like.

The following Experiments further show the analgic and antipyretic activities of the compounds of the present invention.

Experiment I.

To Wistar strain male rats having about 300 – 350 grs. body weight, an aqueous suspension of yeast was subcutaneously injected to induce pyrexia.

At the lapse of 4 hours since the dose of the yeast suspension, the compounds under test given in hereinaftermentioned Table 10 in a form of suspension in a 5% gum arabic aqueous solution are orally administered. The rectal temperatures of the rats were measured periodically by means of a thermister-type thermometer sold by Japan Koden K.K. As control, said 5% gum arabic aqueous solution alone was administered. In Table 10 later given, "Change in rectal temperature" shows the differences between the body temperatures measured at the time before and after the oral administrations of the compounds.

From the data given in Table 10, it is evident that the compound (5) of the present invention had tendency of an antipyretic activity with 1.25mg/kg p.o.; with 5mmg/kg.p.o., a significant antipyretic activity appeared at one hour lapse since the administration; and with 20 mg/kg P.O., the maximum antipyretic activity was attained. With the increased administrations up to 80 and 160 mg/kg.P.O., there were, however, observed no body temperatures lower than the normal body temperatures.

Fenoprofen and Ibuprofen as the compounds for comparison, exhibited an apparent antipyretic activity, when the compounds were administered in an amount over 5 mg/kg.P.O.; the maximum antipyretic activities were gained at the administration of 20 mg/kg.P.O.

With Aspirin, on the other hand, a significant antipyretic activity was observed when 320 mg/kg.P.O. were administered; a significant antipyretic activity was observed at 80 mg/kg. P.O.; and at 320 mg/kg.P.O., the body temperature injuriously depressed below the normal body temperature.

The results of observation are summarized in Table 10 later given.

From the data in Table 10, it is apparent that the compound of the present invention possesses an excellent antipyretic activity in 10 – 15 times stronger than Aspirin; the activity is comparable to those of the known Fenoprofen and Ibuprofen.

Experiment J.

Analgesic activity of the compound of the present invention in comparison with the known compounds.

Analgesic activity of the compound was tested as the measure of antagonism to writhing syndrome appeared when 0.1 ml/10g of 0.7% acetic acid was intraperitoneally injected to the dd strain male mice having 17 – 20 grs. body weight which had been abstinence from food for 18 hours.

The compounds under test were orally administered in a form of suspension in a 5% aqueous solution of gum arabic. After one hour from the administration, the onset times required for the writhing syndrome were scored.

In another Experiment in the combined use of the compounds under test and Codeine phosphate, 10 – 20 mg/kg of Codeine phosphate were orally administered immediately after the oral administration of the compounds under test. The results of the observation were listed in Table 11 later given.

From the data in Table 11, it is understood the following facts:

a. In the single administration of the respective compounds, significant antagonisms are observed when the compound (5) of the present invention and Fenoprofen are administered over 20 mg/kg. In the single administration of Ibuprofen, appearance of the significant writhing syndrome is retarded with 80 mg/kg administration, while with Aspirin the significant writhing syndrome is retarded with 160 mg/kg administration.

b. In the combined administration of the compounds in various amounts and Codeine phosphate in an amount of 10 and 20 mg/kg.P.O., enhanced analgesic activities are observed. More particularly, 10 – 80 mg/kg.P.O. of the compound (5) of the present invention in combination with the abovementioned amounts of Codeine, the retardation of the writhing syndrome is observed depending upon the amounts of dosage. The activity is almost equivalent to those of Fenoprofen and Ibuprofen, and far stronger than that of Aspirin.

From the data given in Table 11, it is noted that the compound (5) of the invention possesses a high analgesic activity and imparts an enhancing effect on the analgesic activity of Codeine; said effect is comparable to that of Fenoprofen and slightly stronger than that presented by Ibuprofen.

After all, the abovementioned several pharmacological Experiments come to the conclusion that a. The compounds of this invention possess prominent anti-inflammatory activity and superior to the hitherto known anti-inflammatory substances such as Ibuprofen and Fenoprofen with respect to various pharmacological viewpoints.

b. The compounds of this invention possess analgesic and antipyretic activities comparable to those represented by Ibuprofen and Fenoprofen.

c. The compounds of this invention possess relatively low toxicity comparable to those of Ibuprofen and Fenoprofen, and are far secure as compared with the known compounds which for the time are broadly employed for the therapeutic purposes. In this connection, it is particularly notable that the compounds of this invention exhibit a considerably low gastric irritability.

Since the compounds of this invention, as is stated above, Exhibit excellent analgesic and anti-inflammatory activities, they are useful for therapeutic treatments of the various inflammatory diseases such as rheumatism, arthritic, spondylitis, tendinitis, fracture, distorsion, postoperative inflammation, otitis media, nasosinusitis, neuralgia, lumbago, rachialgia, odontalgia and the like.

The fact is highly appreciated that there is not accompanied with inferior by effects such as tinnitus aurium, hard of hearing and gastrointestinal disturbance, when the compounds of this invention are administered as anti-inflammatory and analgesic agents, contrary to the cases where the known compounds are employed. The compounds may therefore by used advantageously as "minor anti-inflammatory agent" for the treatment of patient that does not particularly endure administration of a severe anti-inflammatory agent or patient of chronic but slight case that requires successive administrations of agent for an elongated period.

The compounds of the invention may usually be orally administrated to the patients in an amount of about 600 – 1200 mg/day.

Following examples will serve to illustrate the invention.

Example 1

Synthesis of 2-[m-(o-chlorophenoxy)phenyl]propionic acid

12 Grs. of 2-[m-(o-chlorophenoxy)phenyl]propionaldehyde are suspended in 100 ml of a 50% acetic acid, and under cooling with tap-water, there are added portionwise 11 grs. of pulverized potassium permanganate for 2 hours. During the addition of the permanganate, the temperature of the reaction mixture is kept below 30° C. When the addition of the permanganate is over, the entire mixture is stirred for 3 hours. The reaction mixture, after dissolution of precipitated manganese dioxide with addition of sodium hydrogen sulfite, is extracted with benzene. The benzene extract is brought to alkaline by the addition of an aqueous caustic soda solution. Aqueous layer separates out is recovered and brought to acidic by the addition of hydrochloric acid and extracted again with benzene. The benzene extract recovered is dried on Glauber's salt, and the benzene is removed by distillation. The residue of the distillation is distilled under reduced pressure to obtain a fraction distilling out at 185° – 187° C./0.8 mmHg which is the purposed product in a form of colorless and viscus oily substance amounting to 9.2 grs.

Elementary analysis for $C_{15}H_{13}ClO_3$ gives:

|  | C | H |
|---|---|---|
| Calculated (%) | 65.10 | 4.74 |
| Found (%) | 65.45 | 4.69 |

2-[m-(o-chlorophenoxy)phenyl]propionaldehyde used as starting material in the above example may be prepared as follows:

a. Synthesis of ethyl ester of 3-[m-(o-chlorophenoxy)phenyl]-2,3-epoxybutylic acid To the solution of 13.8 grs. of metallic sodium in 300 ml of ethanol under ice-cooling, there are gradually added 50 ml. of an ethanolic solution containing 50 grs. of 3-(o-chlorophenoxy)acetophenone (B. P. 151° –159° C./0.11 mmHg) and 49 grs. of ethyl ester of chloroacetic acid. After completion of the addition, the mixture is stirred under that condition and then after stirred at room temperature for 3 hours is refluxed for 1 hour. The resulting reaction mixture is concentrated to until a ⅓ volume of the original and dissolved in 300 ml of benzene. The benzene solution was washed 3 times with water, dried on Glauber's salt, and the benzene is distilled off. The residue is subjected to distillation under reduced pressure to obtain 56 grs. of the purposed product having the boiling point of 188° –192° C./1.1 mmHg.

Elementary analysis of the product for $C_{18}H_{17}ClO_4$ gives:

|  | C | H |
|---|---|---|
| Calculated (%) | 64.97 | 5.15 |
| Found (%) | 64.86 | 5.25 | b. Synthesis of 3-[m-(o-chlorophenoxy)phenyl]-2,3-epoxybutylic acid

25 Grs. of ethyl ester of 3-[m-(o-chlorophenoxy)-phenyl]-2,3-epoxybutylic acid are added to 150 ml of ethanol containing 10 grs. of caustic soda, and the mixture is refluxed for 2 hours. The resulting reaction mixture is concentrated, and 200 ml of water are added thereto. The mixture is shaken with 100 ml of benzene, and the aqueous layer separates out is recovered, which is made acidic with addition of hydrochloric acid and extracted with benzene. The benzene extract is dried on Glauber's salt, and the benzene is distilled off from the extract. There are thus obtained 22.8 grs. of the purposed product in a form of viscous oily substance.

c. Synthesis of 2-[m-(o-chlorophenoxy)-phenyl]propionaldehyde 22.8 Grs. of 3-[m-(o-chlorophenoxy)phenyl]-2,3-epoxy butylic acid are introduced into a 6% hydrochloric acid and the solution is refluxed under stirring for 3 hours to complete the reaction. The reaction mixture is extracted with benzene and the extract is washed with water and dried on Glauber's salt. The benzene is distilled off and the residue is subjected to distillation under reduced pressure to collect 13.6 grs. of the fraction as the intended product having the boiling point of 170.5° – 175.5° C. The product is a viscous oily substance.

Elementary analysis of the product for $C_{15}H_{15}ClO_2$ gives:

|  | C | H |
|---|---|---|
| Calculated (%) | 69.10 | 5.03 |
| Found (%) | 68.89 | 5.10 |

EXAMPLE 2

Synthesis of aluminium salt of 2-[m-(p-chlorophenoxy)phenyl]propionic acid

To a solution of 2.9 grs. of metallic sodium in 100 ml of isopropanol under ice-water cooling, there are gradually added drop by drop a solution prepared by dissolution of 17.4 grs. of 3-(p-chlorophenoxy)acetophenone and 16.2 grs. of ethyl ester of monochloroacetic acid and the total is made finally to 50 ml. When addition is completed, the mixture is stirred at room temperature for 4 hours and for one hour under heat. The reaction mixture is concentrated to a half of the original volume. 100 ml of toluene are added to the concentrate. The toluene layer is recovered by separation, washed with water, dried on Glauber's salt, and concentrated to obtain 23 grs. of a colorless oily substance. To the product, there are added 50 ml of ethanol which contains 2.3 grs. of caustic soda, and the mixture is refluxed for 30 minutes.

The reaction liquor is subjected to distillation under reduced pressure and 100 ml of a 12% hydrochloric acid are added to the residue, which is then refluxed for 5 hours. After cooling, the reaction liquor is extracted with benzene. The benzene extract is washed with water and a dilute aqueous solution of caustic soda and again water, and dried on Glauber's salt. The benzene is removed by distillation from the dry solution to obtain a colorless oily substance which is 2-[m-(p-chlorophenoxy)phenyl]propionaldehyde. The oily substance is dissolved in 120 ml of ethanol, and to the solution. There is added 15 grs. of silver nitrate dissolved in 30 ml of ester. Under stirring there are added dropwise 50 ml of an aqueous solution containing 10 grs. of caustic soda, and when the addition is completed, the whole is refluxed for 1.5 hours. The reaction liquor is filtered and the filtrate is concentrated to a half of the original volume. Water is added to the concentrate and extracted with benzene. The benzene extract is washed with water and dried on Glauber's salt and the benzene is removed by distillation. The residue is subjected to distillation under reduced pressure to collect 6.7 grs. of the fractions having a boiling point of 192° – 194° C./0.8 mmHg. The product, i.e., 2-[m-(p-chlorophenoxy)phenyl]propionic acid, is dissolved in 50 ml of a solution of 2.5 grs. of aluminium isopropoxide in isopropanol, and the whole is warmed for 1 hour. White powdery substance separates out which is recovered by filtration and washed with isopropanol and dried. Yield is 9.7 grs.; melting point is over 300° C.

The product is assumed to be the formula of $(C_{15}H_{13}ClO_3)_2.Al(OH).3H_2O$.

Elementary analysis of said $C_{30}H_{27}Cl_2O_7.Al(OH).3H_2O$ gives:

|  | C | H |
|---|---|---|
| Calculated (%) | 55.48 | 4.81 |
| Found (%) | 55.52 | 4.52 |

EXAMPLE 3

Synthesis of 2-[m-(p-fluorophenoxy)phenyl]propionic acid

2-[m-(p-fluorophenoxy)phenyl]propionaldehyde, which has been synthetically prepared in accordance with Example 1 from 3-(p-fluoro-phenoxyphenyl)acetophenone (boiling point: 137° – 138° C./0.5 mmHg) and ethyl ester of chloroacetic acid, is subjected to oxidation in the manner described in Example 1. There is thus obtained the purposed product in a form of oily substance having the melting point of 175° – 176° C./0.5 mmHg.

Elementary analysis of the product for $C_{15}H_{13}FO_3$ gives:

|  | C | H |
|---|---|---|
| Calculated (%) | 69.22 | 5.04 |
| Found (%) | 68.99 | 5.03 |

The free acid is converted in accordance with Example 2 into the corresponding aluminium salt in a white powdery form. The product is assumed to be $(C_{15}H_{13}FO_3)_2.Al(OH).2H_2O$.

Elementary analysis of the product for $C_{30}H_{27}F_2O_7.2H_2O$ gives:

|  | C | H |
|---|---|---|
| Calculated (%) | 60.20 | 4.89 |
| Found (%) | 60.22 | 5.06 |

EXAMPLE 4

Synthetic preparation of 2-[m-(p-chloro-o-methylphenoxy)phenyl]propionic acid

2-[m-(p-chloro-o-methyl-phenoxy)phenyl]propionaldehyde, which has been synthesized in accordance with Example 1 from 3-(p-chloro-o-methyl-phenoxyphenyl)acetophenone having the melting point of 148° – 156° C./0.5 mmHg and ethyl ester of chloroacetic acid, is subjected to oxidative treatment in the manner of Example 1 to obtain the contemplated product.

The product is a colorless oily substance having the boiling point of 183° – 185° C./1 mmHg. Elementary analysis of the product, $C_{16}H_{15}ClO_3$, gives:

|  | C | H |
|---|---|---|
| Calculated (%) | 66.10 | 5.20 |
| Found (%) | 65.91 | 4.95 |

The abovementioned free acid is converted in accordance with the teachings of Example 2 to the corresponding white powdery aluminium salt melting at over 300° C. The product is assumed to be $(C_{16}H_{15}ClO_3)_2.Al(OH).3/2H_2O$.

Elementary analysis of the product, $C_{32}H_{31}Cl_2O_7Al.3/2H_2O$, gives:

|  | C | H |
|---|---|---|
| Calculated (%) | 59.08 | 4.96 |
| Found (%) | 59.08 | 4.86 |

The compounds of Examples 5–7 tabulated in the following table are free acids, which are prepared in accordance with the manner disclosed in Example 1 wherein the conversion of said free acids into the corresponding aluminium salts is conducted in accordance with Example 2.

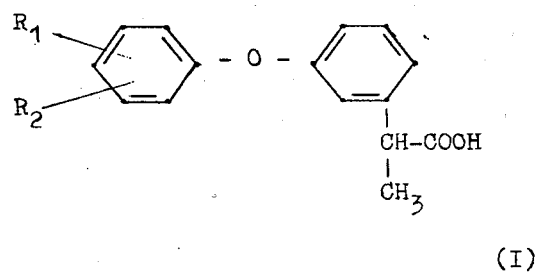

(I)

| Examples | R₁ | R₂ | Chemical formula B.P. (° C./mmHg) | Elementary Analysis Calculated (%) / Found (%) | | Aluminium salt composition (M.P.) | Elementary Analysis Calculated (%) / Found (%) | |
|---|---|---|---|---|---|---|---|---|
|  |  |  |  | C | H |  | C | H |
| 5 | p-CH₃ | H | $C_{16}H_{16}O_3$ (182.5°–184°/0.6) | 4.98 75.12 | 6.29 6.14 | $(C_{16}H_{15}O_3)_2$ Al(OH) 2H₂O (over 300° C.) | 65.07 64.80 | 5.97 5.65 |
| 6 | p-CF₃ | H | $C_{16}H_{13}F_3O_3$ (126°–128°/0.9) | 61.93 62.08 | 4.22 4.10 |  |  |  |
| 7 | p-OCH₃ | H | $C_{16}H_{16}O_4$ | 70.57 | 5.92 |  |  |  |

| | Chemical formula | Elementary Analysis | | Aluminium salt | Elementary Analysis | |
|---|---|---|---|---|---|---|
| | | Calculated (%) | | | Calculated (%) | |
| | B.P. (° C./mmHg) | Found (%) | | composition (M.P.) | Found (%) | |
| Examples R₁ R₂ | | C | H | | C | H |
| | (194°–197°/0.75) | 70.66 | 5.83 | | | |

EXAMPLE 8

Synthesis of 2-[m-(p-chlorophenoxy)phenyl]propionic acid

To 200 ml of a methanolic solution of 14 grs. of caustic potash, there are added 25 grs. of p-chlorophenol. The mixture is evaporated to dryness under reduced pressure. The dry substance is further dried at 120° C. The dry substance and potassium salt of 2-(m-bromophenyl)propionic acid, which has separately been prepared from 12 grs. of caustic potash and 46 grs. of 2-(m-bromophenyl)propionic acid, are together dissolved in 300 ml of dimethyl formamide. To the solution, there are added one gr. of pulverized metallic copper and 0.5 grs. of cuprous iodide, and the mixture is refluxed for 18 hours. The reaction mixture is concentrated, and 500 ml of water are added to the residue. The mixture is percolated through cerite, and the filtrate is made acidic with hydrochloric acid. Oily substance separates out is extracted with benzene and the benzene extract is washed with water, dried on Glauber's salt and the solvent is distilled off. The residue is distilled under reduced pressure to collect 26.8 grs. of the fractions boiling at 192° to 194° C./0.8 mmHg., which are the purposed product. Elementary analysis of the substance for $C_{15}H_{13}ClO_3$ gives:

| | C | H |
|---|---|---|
| Calculated (%) | 65.10 | 4.74 |
| Found (%) | 65.37 | 4.71 |

2-(m-Bromophenyl)propionic acid used as starting material may be synthesized as follows:

m-Bromophenyl acetic acid ethyl ester is dissolved in an ethanol solution of sodium ethylate. To the solution there is added carbonic ethyl ester and the whole is refluxed. After completion of the reaction, the solvent is removed by distillation, and the residue is distilled under reduced pressure to collect m-bromophenyl malonic ethyl ester as the fraction having the boiling point of 134°–139° C. Said m-bromophenyl malonic acid ethyl ester is dissolved in ethanol, and sodium ethylate is added thereinto. To the resulting solution, there is added under stirring methyl iodide and the whole is refluxed. The reaction mixture is concentrated to ⅓ of its original volume, and there is added an alcoholic solution of potassium hydroxide. The mixture is refluxed, and the reaction liquor is concentrated and the water is added to the residue and brought to acidic with hydrochloric acid. Oily substance separates out is extracted with benzene; the benzene extract is washed with water, dried on Glauber's salt and the solvent is removed by distillation. The residue is distilled under reduced pressure to collect the fraction boiling at 131°–132° C./0.6 mmHg as the purposed product. The product is a viscous oily substance. Elementary analysis of the product for $C_9H_9BrO_2$ gives:

| | C | H |
|---|---|---|
| Calculated (%) | 47.18 | 3.96 |
| Found (%) | 47.10 | 3.80 |

EXAMPLE 9

Synthesis of 2-[m-(p-chloro-o-methyl-phenoxy)phenyl]-propionic acid

14 Grs. of p-chloro-o-cresol are dissolved in 100 ml of methanol solution of 6.2 grs. of potassium hydroxide, and the solution is evaporated to dryness under reduced pressure. The substance is further dried at 120° C.

A solution separately prepared by dissolving 23 grs. of 2-(m-bromophenyl)propionic acid in 100 ml of methanolic solution of 6.2 grs. of potassium hydroxide is evaporated to dryness under reduced pressure. The substance is further dried at 120° C.

The two dry substances thus obtained are together dissolved in 200 ml of dimethyl sulfoxide, and to the resulting solution, there are added 0.5 grs. of pulverized metallic copper and 0.2 grs. of cuprous iodide. The mixture is subjected to reaction with stirring at 170° C. for 15 hours. The reaction mixture is percolated through cerite, and the filtrate is concentrated under reduced pressure to a half volume of the original. Water is added to the concentrate and shaked with benzene. Aqueous layer is recovered, made acidic with hydrochloric acid, and an oily substance that separates out is extracted with chloroform.

The chloroform extract is washed with water, dried on Glauber's salt and distilled to remove the solvent. The residue is distilled under reduced pressure to collect 15.2 grs. of the fraction boiling at 183°–185° C./1 mmHg, the purposed product. The product is a colorless, viscous oily substance. Elementary analysis of the product for $C_{16}H_{15}ClO_3$ gives:

| | C | H |
|---|---|---|
| Calculated (%) | 66.10 | 5.20 |
| Found (%) | 65.93 | 5.17 |

The product may be converted into its aluminium salt as follows:

The product is dissolved in isopropanol, and to the solution, there is added drop by drop under stirring an isopropanol solution of aluminium isopropoxide. White powdery substance separates out is recovered by filtration and dried by weathering. The substance thus obtained has the melting point over 300° C., which is presumed as the formula: $(C_{14}H_{15}ClO_5)_2.Al(OH).3/2-H_2O$ Elementary analysis of this compound, $C_{32}H_{31}Cl_2O_7.Al.3/2H_2O$, gives:

|  | C | H |
|---|---|---|
| Calculated (%) | 59.08 | 4.96 |
| Found (%) | 59.05 | 4.93 |

2-(m-Hydroxy-phenyl)propionic acid used as the starting material may be prepared as follows:

To an ethanol solution prepared by dissolving sodium ethylate and m-benzyloxy-acetophenone, there is added an ethanolic solution containing chloroacetic ethyl ester. The whole is stirred for one hour and then refluxed for 1 hour. The reaction liquor is concentrated to a ⅓ volume of the original and dissolved in benzene. The resulting solution is washed with water, dried on Glauber's salt and the benzene is distilled off therefrom. The residue is a crude 3-(m-benzyloxyphenyl)-2,3-epoxybutylic ethyl ester.

This residue is introduced to an ethanolic solution of potassium hydroxide and the whole is refluxed for 2 hours. The reaction mixture is concentrated to a ⅓ volume of the original, and water and then benzene are added with shaking. The aqueous layer is recovered by separation which is made acidic with hydrochloric acid. An oily substance separates out is extracted with benzene; the benzene extract is washed with water and dried on Glauber's salt. The benzene is distilled off to obtain the residue which is a crude 3-(m-benzyloxyphenyl)-2,3-epoxy-acetic acid.

The residue is dissolved in a 6% hydrochloric acid and the solution is refluxed for 3 hours and then extracted with benzene. The benzene extract is washed with water and dried on Glauber's salt. The residue remained by distilling off of the solvent is a crude 2-(m-benzyloxyphenyl)propionaldehyde.

This residue is suspended in a 50% acetic acid, and to the solution, there is added in small portions under water-cooling pulverized potassium permanganate. During the addition, the reaction temperature is kept below 30° C. When the addition of permanganate is completed, the reaction mixture is stirried at room temperature for 3 hours. Sodium hydrogen sulfite is added to the reaction mixture in order to dissolve mangan dioxide separated out. The reaction mixture is extracted with benzene and the extract is brought to alkaline by adding an aqueous solution of caustic soda. Aqueous layer separates out is recovered which is made acidic by means of hydrochloric acid and extracted again with benzene. The benzene extract is washed with water and dried on Glauber's salt and the benzene is removed by distillation. Residue is recrystallized from a mixed solvent consisting of acetone and hexane. There is thus obtained 2-(m-benzyloxyphenyl)propionic acid having the melting point of 117°–118° C.

2-(m-Benzyloxyphenyl)propionic acid obtained in the preceding paragraph is dissolved in ethanol, added thereinto 5%-palladium-carbon and subjected to catalytic reduction. When the reduction is completed, the spent catalyst is removed by filtration and the filtrate is distilled under reduced pressure to remove the ethanol. The residue is distilled under reduced pressure to collect the fractions boiling at 145°–157° C/0.6 mmHg, to obtain the purposed 2-(m-hydroxyphenyl)propionic acid.

EXAMPLE 10

Synthesis of 2-/m-(o-chlorophenoxy)phenyl/propionic acid 2-(m-Hydroxyphenyl)propionic acid is subjected to reaction with o-chloro-bromo-benzene in accordance with the teaching of Example 9. Fractional distillates having the boiling point of 185°–187° C/0.8 mmHg are collected which is the intended product. Elementary analysis of the product for $C_{15}H_{13}ClO_3$ gives:

|  | C | H |
|---|---|---|
| Calculated (%) | 65.10 | 4.74 |
| Found (%) | 65.27 | 4.58 |

The compounds obtained by Examples 11–14 are prepared in the same manner as disclosed in Example 9. The elementary analysis of these compounds is shown in the following Table.

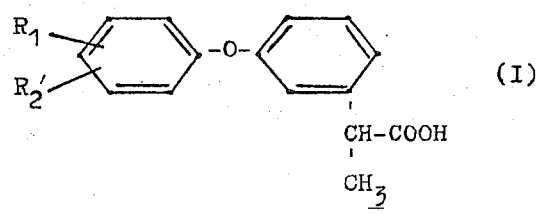

(I)

| Examples | $R_1$ | $R_2$ | Chemical formula B.P. (°C./mmHg) | Elementary Analysis Calculated (%) Found (%) | | Aluminium salt composition (M. P.,°C.) | Elementary Analysis Calculated (%) Found (%) | |
|---|---|---|---|---|---|---|---|---|
|  |  |  |  | C | H |  | C | H |
| 11 | p-CH$_3$ | H | $C_{16}H_{16}O_3$ (182.5°–184°/0.6) | 74.98 75.03 | 6.29 6.10 | $(C_{16}H_{16}O_3)_2\cdot Al(OH)\cdot 2H_2O$ (over 300°C.) | 65.07 64.93 | 5.97 5.78 |
| 12 | p-F | H | $C_{15}H_{13}FO_3$ (175°–176°/0.5) | 69.22 69.17 | 5.04 5.10 | $(C_{15}H_{13}FO_3)_2\cdot Al(OH)\cdot 2H_2O$ (over 300°C.) | 60.20 60.27 | 4.89 5.09 |
| 13 | p-CF$_3$ | H | $C_{16}H_{13}F_3O_3$ (126°–128°/0.9) | 61.93 61.87 | 4.22 4.19 |  |  |  |
| 14 | p-OCH$_3$ | H | $C_{16}H_{16}O_4$ (194°–197°/0.75) | 70.57 70.64 | 5.92 5.91 |  |  |  |

EXAMPLE 15

Synthesis of 2-[m-(p-chlorophenoxyphenyl)]propionic acid

13 Grs. of 3-(p-chlorophenoxy)phenyl acetic acid having M. P. of 46.5°–47.5° c. are subjected to reaction in the presence of metallic sodium with 50 ml of carbonic acid ethyl ester to obtain 2-[m-(p-chlorophenoxyphenyl)]malonic acid ethyl ester.

The malonic acid ethyl ester is dissolved in 50 ml of ethanolic solution which contains 1.2 grs. of metallic sodium. To the resulting solution, there are added 14 grs. of methyl iodide under stirring at room temperature. Stirring is continued for further 1 hour and the reaction mixture is refluxed for 3 hours. To the reaction mixture, there are then added 30 ml of 5n-aqueous solution of caustic soda and 20 ml of water. The mixture after refluxed for 3 hours is concentrated under reduced pressure. Water is added to the residue, and the mixture is brought to acidic by means of hydrochloric acid and extracted 3 times with ether. The collected etheral extract is washed with water, dried and subjected to distillation to remove ether. The residue thus obtained is distilled under reduced pressure to obtain 9.4 grs. of the intended product in a colorless viscous oil by collecting fractions boiling at 192° – 194° C./0.8 mmHg.

Elementary analysis of the product for $C_{15}H_{13}ClO_3$ gives:

|  | C | H |
|---|---|---|
| Calculated (%) | 65.10 | 4.74 |
| Found (%) | 65.40 | 4.65 |

The compound thus obtained is dissolved in 50 ml of isopropanol. The solution, after addition under stirring 50 ml of a solution containing 2.5 grs. of aluminium isopropoxide in isopropanol, is warmed for one hour. White powdery substance separates out is corrected by filtration, washed with isopropanol and dried. Yield: 9.7 grs.; M. P. over 300° C. The compound is assumed to be $(C_{15}H_{13}ClO_3)_2 \cdot Al(OH) \cdot 3H_2O$.

Elementary analysis of the compound for $C_{30}H_{27}Cl_2O_7 \cdot Al \cdot 3H_2O$ gives:

|  | C | H |
|---|---|---|
| Calculated (%) | 55.48 | 4.81 |
| Found (%) | 55.52 | 4.52 |

EXAMPLE 16

Synthesis of 2-[m-(o-chlorophenoxyphenyl)]propionic acid

2-Cyano-α-[m-(o-chlorophenoxyphenyl)] acetic acid ethyl ester having the boiling point of 182° – 194° C./mmHg, which has been prepared by the reaction in the presence of metallic sodium of 12 grs. of 3-(o-chlorophenoxy)phenyl acetonitrile boiling at 158° – 167° C./0.9 mmHg and 5.4 grs. of chlorocarbonic acid ethyl ester, is dissolved in 70 ml of ethanol solution containing 1.2 grs. of metallic sodium. To the solution there are added 12 grs. of methyl iodide under stirring at room temperature. The mixture after again is stirred for 1 hour, refluxed for 4 hours. The reaction mixture is concentrated by evaporation, and water is added to the residue of distillation and extracted three times with ether. The combined etheral extract is washed and, after drying, the ether is removed by distillation. There is obtained a yellow oily residue. To the latter, there are added 80 ml of an ethanol solution which contains 6 grs. of caustic alkali, and the resulting mixture is refluxed for 5 hours. After addition of 15 ml of a 50% aqueous solution of caustic potash, the reaction mixture is again refluxed for 5 hours, and is then concentrated; water is added to the concentrate, made acidic by the addition of hydrochloric acid and extracted with ether. The etheral extract is washed with water, dried and distilled under reduced pressure to collect the fractions boiling at 175° – 185° C./0.5 mmHg as the purposed product.

Yield: 14.5 grs.

Elementary analysis of the product for $C_{15}H_{13}ClO_3$ gives:

|  | C | H |
|---|---|---|
| Calculated (%) | 65.10 | 4.74 |
| Found (%) | 65.45 | 4.69 |

The resulting compound is converted in accordance to Example 15 into its aluminium salt having the melting point over 300° C. The product is assumed to be $(C_{15}H_{13}ClO_3)_2 \cdot Al(OH) \cdot 3H_2O$.

Elementary analysis of the product for $C_{30}H_{27}Cl_2O_7 \cdot Al \cdot 3H_2O$ gives:

|  | C | H |
|---|---|---|
| Calculated (%) | 55.48 | 4.81 |
| Found (%) | 55.64 | 4.91 |

The products of further Examples 17–20 obtained in accordance with the procedures disclosed in the preceding Example 16. Elementary analysis of these products are shown in the following Table.

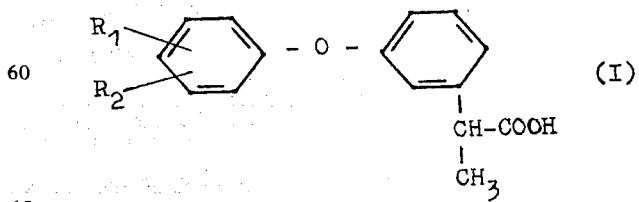

| Examples | $R_1$ | $R_2$ | Chemical formula B.P. (°C./mmHg) | Elementary analysis Calculated (%) / Found (%) C | H | Aluminium salt composition (M. P.) | Elementary analysis Calculated (%) / Found (%) C | H |
|---|---|---|---|---|---|---|---|---|
| 17 | p-CH$_3$ | H | C$_{16}$H$_{16}$O$_3$ (182.5°–184°/0.6) | 74.98 / 75.12 | 6.29 / 6.14 | (C$_{16}$H$_{16}$O$_3$)$_2$·Al(OH)·2H$_2$O (over 300 °C.) | 65.07 / 64.80 | 5.97 / 5.65 |
| 18 | p-CF$_3$ | H | C$_{16}$H$_{13}$F$_3$O$_3$ (126°–128°/0.9) | 61.93 / 62.08 | 4.22 / 4.10 | | | |
| 19 | p-OCH$_3$ | H | C$_{16}$H$_{16}$O$_4$ (194°–197°/0.75) | 70.57 / 70.66 | 5.92 / 5.83 | | | |
| 20 | p-Cl | —OCH$_3$ | C$_{16}$H$_{15}$ClO$_3$ (183°–185°/1) | 66.10 / 65.91 | 5.20 / 4.95 | (C$_{16}$H$_{15}$ClO$_3$)$_2$·Al(OH)·3H$_2$O (over 300°C.) | 59.08 / 59.08 | 4.96 / 4.86 |

EXAMPLE 21

Preparation of 2-[m-(o-Chlorophenoxy)phenyl]-propionic acid 10.7 Grs. of matellic magnesium shavings are immersed in 150 ml of dry ether held in 1 liter capacity of 4-neck flask. To the content of the flask under nitrogen atmosphere, there are added drop by drop with stirring 66 ml of a dry etheral solution containing 125 grs. of 1-[m-(o-chlorophenoxy)]-phenethyl bromide. Commencement of the reaction may be facilitated, if necessary, by adding a few drops of methyl iodide to the reaction mixture. A vigorous reaction which takes place with foaming and with a slight heat-evolution may be controlled suitably by regulated addition of said etheral solution so that a mild reflux of the reaction medium will take place. About 1.5 hours will be required for completion of the addition.

The reaction mixture is then warmed to reflux. When most of the magnesium flakes are disappeared after about 3 hours of the reaction time, the reaction mixture, that is, Grignard solution, is cooled.

To 400 ml of dry ether held in another 4-neck flask of 2 liter-capacity, there is introduced 700 grs. of pulverized dry-ice with vigorous stirring to form a dry ice suspension.

To the suspension, there is added drop by drop for about 20 minutes the Grignard solution obtained in the preceding paragraph. The resulting reaction mixture under continuous stirring is held to evaporate up an excess of the dry ice remained.

A small quantity of ice-water is first added to the reaction mixture and then 200 ml of a 20% hydrochloric acid.

Supernant etheral layer is recovered, washed with water and shaked twice each 200 ml of a 20% potassium carbonate solution. The aqueous layer is recovered, which is then made acidic by means of hydrochloric acid and extracted with ether. The etheral layer is washed with water, dried on solid magnesium sulfate. The ether is then removed therefrom by distillation.

There are obtained 82.2 grs. of a viscous oily substance boiling at 215°–225° C. amounting to 72% of yield.

Elementary analysis of the compound for C$_{15}$H$_{13}$ClO$_3$ gives:

|  | C | H |
|---|---|---|
| Calculated (%) | 65.10 | 4.74 |
| Found (%) | 65.38 | 4.77 |

1-[m-(o-Chlorophenoxy)]phenethyl bromide employed as the starting material in this Example may be prepared by the following reaction steps.

m-(o-Chlorophenoxy)acetophenone having the boiling point of 165°–172° C./1.6 mmHg prepared by Ullmann's condensation reaction from 3-bromoacetophenone and 2-chlorophenol is reduced with sodium borohydride to obtain 1-[m-(o-chlorophenoxy)]phenethyl alcohol boiling at 172°–180° C./2 mmHg. 50 Grs. of the product are added drop by drop to 150 ml of a chloroform solution of 21.8 grs. of phosphorus tribromide and the mixture is stirred for 3 hours. 100 Ml of ice-water are added to the reaction mixture, and the lower layer is separated, which is then washed with water, dried and subjected to distillation to remove the solvent. The residue is distilled under reduced pressure to obtain a light yellowish oily substance having the boiling point of 150°–170° C./2.5 mmHg.

The bromide has a tendency of causing a decomposition if degree of the reduced pressure used for the distillation is insufficient. In practice, however, the bromide well dried may directly be employed without purification by distillation as the starting material in the above Example.

EXAMPLE 22

Preparation of 2-[m-(o-chlorophenoxy)phenyl]-propionic acid

In a mixture consisting of 60 ml of water, 100 ml of concentrated sulfuric acid and 100 ml of acetic acid, 84 grs. of 2-[m-(o-chlorophenoxy)phenyl]propionitrile were refluxed at 120° C. for 6 hours. The reaction liquor is poured in 600 ml of water, and the mixture was extracted with benzene. The benzene extract is shaked twice each with 200 ml of a 10 percent caustic soda aqueous solution. The combined caustic soda solution thus obtained is made acidic with concentrated hydrochloric acid, and again extracted with benzene. The benzene extract is dried, evaporated up to dryness, and the residue remained is distilled under reduced pressure. A fraction boiling at 192°–196° C./1.5 mmHg is collected as the intended product as a colorless, viscous oily substance amounting to 70.8 grs. Yield is 78.5%.

Elementary analysis of the product for C$_{15}$H$_{13}$ClO$_3$ gives:

|  | C | H |
|---|---|---|
| Calculated (%) | 65.10 | 4.74 |
| Found (%) | 65.45 | 4.69 |

2-[m-(o-Chlorophenoxy)phenyl]propionitrile employed as the starting material in the above Example is that prepared as follows: m-(o-Chlorophenoxy)acetophenon (B.P.: 165°–172° C./1.7 mmHg) synthesized by Ullmann's reaction from 3-bromoacetophenone and 2-chlorophenol is reduced with sodium borohydride to obtain 1-[m-(o-chlorophenoxy)]phenethyl alcohol having the boiling point of 172°–180° C./2 mmHg.

50 Grs. of the product are added drop by drop into 150 ml of chloroform which contains 21.8 grs. of phosphorus tribromide. The mixture is stirred at room temperature for 3 hours. Ice-water is then added to the mixture. The lower chloroform layer is recovered, washed with water, dried and distilled off the chloroform. There is remained 5 grs. of a light yellowish oily substance. By distillation under reduced pressure of the product, there is obtained 1-[m-(o-chlorophenoxy)]-phenethyl bromide as a fraction boiling at 150°–170° C./2.5 mmHg.

In practice, the product, however, may immediately be used without purification through such a distillation under reduced pressure to the subsequent reaction step as follows:

75 Grs. of said crude bromide compound are added drop by drop to 100 ml of dimethyl sulfoxide containing 12 grs. of sodium cyanide kept at 60° C. Temperature elevation in the reaction system due to exothermic reaction should be controlled so that it does not elevate over 70° C. After completion of the addition, the whole is kept at 70° C. for 5 hours to perform the reaction. An oil substance separates out as the lower layer by adding 500 ml of water to the reaction mixture is recovered as the purposed product. The aqueous layer is once extracted with benzene, and the benzene extract is combined with said oily substance. The mixture is washed with water, dried and subjected to distillation to remove the benzene. There remains 45 grs. of a light yellow oily substance. By distillation under reduced pressure of said oily substance, there are obtained 39 grs. of a colorless oily substance having the boiling point of 171°–182° C./1.9 mmHg.

The resulting substance is 2-[m-(o-chlorophenoxy)-phenyl]-propionitrile, which may be used without purification to the hydrolytic reaction in the abovementioned Example.

EXAMPLE 23

Preparation of
2-[m-(p-chlorophenoxy)phenyl]-propionic acid 39.2 Grs. of 2-[m-(p-chlorophenoxy)phenyl]propionitrile in 150 ml of a 15% caustic soda aqueous solution are refluxed under stirring for 8 hours. Toward the end of the period, the reaction mixture becomes almost transparent.

After cooling, the reaction liquor is shaken with 100 ml of benzene. The aqueous layer is recovered and made acidic with addition of hydrochloric acid. An oily substance separates out is extracted twice with each 100 ml of benzene. The combined benzene extract are washed with water, dried, and the solvent is distilled off therefrom. The residue is subjected to distillation under reduced pressure. There are obtained 31.5 grs. of a colorless viscous liquid boiling at 218°–225° C./4.7 mm Hg (Yield: 74.8 %).

Elementary analysis of the product for $C_{15}H_{13}ClO_3$ gives:

| | C | H |
|---|---|---|
| Calculated (%) | 65.10 | 4.74 |
| Found (%) | 65.40 | 4.65 |

2-[m-(p-Chlorophenoxy)phenyl]propionitrile employed as the starting material in the above Example is also a new substance and may be prepared as follows:

3-(p-Chlorophenoxy)acetophenone having the boiling point of 167°–172° C./1.3 mmHg which has been prepared by condensation of p-chlorophenol and m-bromoacetophenone in accordance with Ullmann's reaction is reduced with sodium borohydride to 1-[m-(p-chlorophenoxy)]phenethyl alcohol boiling at 170°–175° C./2.0 mmHg.

59.2 Grs. of said 1-[m-(p-chlorophenoxy)]phenethyl alcohol are subjected to bromination in chloroform with 26 grs. of phosphorus tribromide to obtain 67 grs. of crude 1-[m-(p-chlorophenoxy)]phenetylbromide.

The product is added drop by drop to 200 ml of a dimethylformamide solution containing 14 grs. of sodium cyanide, and the mixture is subjected to reaction at 80° C. for 8 hours. The reaction liquor is concentrated, 200 ml of water are added thereto and the mixture is extracted twice with benzene. The combined benzene extracts are washed with water, dried, concentrated and distilled under reduced pressure to collect the fractions having the boiling point of 181°–192° C./3.2 mmHg.

The product amounts to yield of 39.2% is 2-[m-(p-chlorophenoxy)phenyl]propionitrile. (Yield of which based on the intermediate phenethyl alcohol is 63.9%.)

EXAMPLE 24

Preparation of calcium salt of
2-[m-(p-chlorophenoxy)phenyl]propionic acid

21 Grs. of crude 2-[m-(p-chlorophenoxy)phenyl]-propionic acid obtained in Example 23 are dissolved in 300 ml of ethanol. To the resulting solution, there are added 3 grs. of caustic soda dissolved in 30 ml of water and the mixture is evaporated up under reduced pressure to dryness. The residue recovered is recrystallized from 15 ml of ethyl acetate to obtain 21 grs. of the corresponding sodium salt melting at 62°–64° C.

The salt is dissolved in 200 ml of water, and 6 grs. of calcium chloride dissolved in 30 ml of water are added thereinto. White precipitate separates out is recovered by filtration and the same is recrystallized from a 60% ethanol. There are obtained 16 grs. of a white crystal having the melting point of 145°–148° C.

Elementary analysis of the product for $(C_{15}H_{12}O_3Cl)_2$-Ca.3/2$H_2O$ gives:

| | C | H |
|---|---|---|
| Calculated (%) | 58.25 | 4.73 |
| Found (%) | 57.90 | 4.53 |

Table 2

| Compound administered | Oral dose mg/kg | Edema density ± S.E. | % of Inhibition |
|---|---|---|---|
| Control | | .542 ± .018 | |
| | 2.0 | .417 ± .032 | 23 |
| (1) | 10.0 | .323 ± .075 | 40 |
| | 50.0 | .300 ± .045 | 44 |
| | 1.6 | .478 ± .069 | 12 |

INHIBITORY ACTIVITY ON CARRAGEENIN-INDUCED EDEMA IN RATS

TABLE 2 – Continued

INHIBITORY ACTIVITY ON CARRAGEENIN-INDUCED EDEMA IN RATS

| Compound administered | Oral dose mg/kg | Edema density ± S.E. | % of Inhibition |
|---|---|---|---|
| (2) | 8.0 | .373 ± .039 | 31 |
|  | 10.0 | .352 ± .063 | 35 |
|  | 3.2 | .430 ± .068 | 20 |
| (3) | 16.0 | .364 ± .054 | 33 |
|  | 80.0 | .334 ± .055 | 38 |
|  | 1.6 | .544 ± .048 | — |
| (4) | 8.0 | .477 ± .049 | 12 |
|  | 40.0 | .293 ± .056 | 46 |
|  | 1.6 | .371 ± .070 | 31 |
| (5) | 8.0 | .305 ± .044 | 43 |
|  | 40.0 | .250 ± .049 | 53 |
|  | 2.0 | .434 ± .114 | 20 |
| (6) | 10.0 | .412 ± .113 | 24 |
|  | 50.0 | .203 ± .048 | 63 |
|  | 2.0 | .422 ± .040 | 22 |
| (7) | 10.0 | .418 ± .038 | 23 |
|  | 50.0 | .368 ± .073 | 32 |

Table 3

INHIBITORY ACTIVITY ON KAOLIN-INDUCED EDEMA IN RATS

| Compound administered | Oral dose mg/kg | After 3 hrs. Edema D. S.E. | % of I.* | After 5 hrs. Edema D. S.E. | % of I.* | After 7 hrs. Edema D. S.E. | % of I.* |
|---|---|---|---|---|---|---|---|
| Control | — | .420 ± .016 | — | .564 ± .028 | — | .607 ± .037 | — |
| Ibuprofen | 8 | .313 ± .093 | 25 | .450 ± .075 | 20 | .571 ± .046 | 6 |
|  | 40 | .267 ± .055 | 36 | .401 ± .068 | 29 | .514 ± .105 | 15 |
| (1) | 10 | .313 ± .016 | 25 | .406 ± .019 | 28 | .560 ± .017 | 8 |
|  | 50 | .245 ± .050 | 42 | .272 ± .053 | 52 | .356 ± .065 | 41 |
| (2) | 8 | .418 ± .040 | — | .499 ± .048 | 11 | .612 ± .067 | — |
|  | 40 | .212 ± .023 | 49 | .292 ± .031 | 48 | .406 ± .057 | 33 |
| (3) | 16 | .418 ± .024 | — | .491 ± .021 | 13 | .524 ± .037 | 14 |
|  | 80 | .297 ± .085 | 29 | .340 ± .107 | 40 | .442 ± .119 | 27 |
| (4) | 8 | .369 ± .048 | 12 | .519 ± .035 | 8 | .625 ± .040 | −3 |
|  | 40 | .271 ± .075 | 35 | .333 ± .073 | 41 | .396 ± .072 | 35 |
| (5) | 8 | .334 ± .069 | 20 | .442 ± .045 | 21 | .563 ± .060 | 7 |
|  | 40 | .201 ± .021 | 52 | .245 ± .017 | 57 | .294 ± .035 | 51 |
| (6) | 10 | .308 ± .025 | 27 | .384 ± .025 | 32 | .515 ± .041 | 15 |
|  | 50 | .215 ± .024 | 49 | .280 35 .021 | 50 | .365 ± .025 | 40 |
| (7) | 10 | .393 ± .047 | 6 | .496 ± .045 | 12 | .568 ± .046 | 6 |
|  | 50 | .386 ± .050 | 8 | .473 ± .040 | 16 | .555 ± .035 | 8 |

*% of I.: % of Inhibition

Table 4

INHIBITORY ACTIVITY ON DEXTRAN-INDUCED EDEMA IN RATS

| Compound administered | Oral dose mg/kg | After 2 hrs. Edema D. S.E. | % of I.* | After 3 hrs. Edema D. S.E. | % of I.* |
|---|---|---|---|---|---|
| Control | — | .838 ± .066 | — | .753 ± .049 | — |
|  | 8 | .791 ± .038 | 5 | .683 ± .024 | 9 |
| Ibuprofen | 40 | .760 ± .075 | 9 | .705 ± .056 | 6 |
| (1) | 10 | .771 ± .022 | 8 | .710 ± .036 | 5 |
|  | 50 | .751 ± .060 | 10 | .631 ± .025 | 16 |
| (2) | 8 | .795 ± .031 | 5 | .749 ± .026 | 1 |
|  | 40 | .846 ± .013 | 1 | .773 ± .027 | −3 |
| (3) | 16 | .782 ± .062 | 6 | .713 ± .036 | 5 |
|  | 80 | .776 ± .022 | 7 | .723 ± .027 | 4 |
| (4) | 8 | .753 ± .052 | 10 | .780 ± .033 | 10 |
|  | 40 | .780 ± .033 | 6 | .692 ± .048 | 8 |
| (5) | 8 | .830 ± .052 | 1 | .746 ± .026 | 1 |
|  | 40 | .742 ± .037 | 11 | .689 ± .035 | 8 |
| (6) | 10 | .818 ± .047 | 2 | .765 ± .043 | 1 |
|  | 50 | .754 ± .051 | 10 | .637 ± .022 | 15 |
| (7) | 10 | .736 ± .038 | 12 | .693 ± .037 | 8 |
|  | 50 | .750 ± .073 | 10 | .707 ± .053 | 6 |

*% of I.: % of Inhibition

Table 5

INHIBITORY ACTIVITY ON ARRS-INDUCED EDEMA IN RATS

| Compound administered | Oral dose mg/kg | After 2 hrs. Edema D. S.E. | % of I.* | After 3 hrs. Edema D. S.E. | % of I.* |
|---|---|---|---|---|---|
| Control | — | .687 ± .017 | — | .716 ± 0.19 | — |
|  | 8 | .615 ± .062 | 10 | .627 ± .049 | 12 |
| Ibuprofen | 40 | .608 ± .047 | 10 | .520 ± .026 | 27 |
| (1) | 10 | .593 ± .053 | 13 | .620 ± .053 | 15 |
|  | 50 | .620 ± .053 | 9 | .566 ± .036 | 21 |
| (2) | 8 | .634 ± .048 | 7 | .599 ± .040 | 16 |
|  | 40 | .553 ± .038 | 19 | .531 ± .026 | 26 |
| (3) | 16 | .613 ± .054 | 10 | .599 ± .065 | 16 |
|  | 80 | .672 ± .036 | 1 | .634 ± .016 | 11 |
| (4) | 8 | .649 ± .032 | 5 | .621 ± .058 | 13 |
|  | 40 | .563 ± .016 | 17 | .535 ± .027 | 25 |
| (5) | 8 | .631 ± .040 | 7 | .637 ± .074 | 11 |
|  | 40 | .610 ± .067 | 10 | .575 ± .074 | 19 |
| (6) | 10 | .659 ± .046 | 3 | .652 ± .053 | 9 |
|  | 50 | .592 ± .033 | 13 | .592 ± .032 | 17 |
| (7) | 10 | .661 ± .085 | 3 | .608 ± .076 | 15 |
|  | 50 | .601 ± .035 | 12 | .581 ± .054 | 19 |

*% of I.: % of Inhibition

Table 6

Inhibitory Activity of Compound (5) and Ibuprofen on Adjuvant-Induced Arthritis in Rats

| Compound administered | Initial Score Total L/R | Initial Score Mean L/R | Initial Paw Volume L/R | Final Score Total L/R | Final Score Mean L/R | Final Paw Volume L/R |
|---|---|---|---|---|---|---|
| Control | 11/18 | 2.2/3.6 | 43/72 | 13/19 | 2.6/3.8 | 55/80 |
| Ibuprofen | 9/19 | 1.8/3.8 | 37/75 | 11/19 | 2.2/3.8 | 52/79 |
| (5) | 9/18 | 1.8/3.6 | 39/73 | 9/16 | 1.8/3.2 | 45/66 |

Daily dosage: 40 mg/kg
R: right paw
L: left paw

Table 7

COMPARATIVE ASSEY ON TEST COMPOUNDS AGAINST IBUPROFEN BY THE FORMALIN-FILTERPAPER-PELLET METHOD*

| Compound administered | Daily dosage (mg/Kg) | Granuloma-Wet-Weight (mm) ± S.E. | Adrenal (mg) | Thymus (mg) |
|---|---|---|---|---|
| Control | — | 131 ± 18 | 41.0 | 553 |
| Ibuprofen | 8 | Non Effective | 39.2 | 631 |
|  | 40 | Non Effective | 34.3 | 471 |
|  | 10 | 114 ± 15 | 37.2 | 588 |
| (1) | 50 | 114 ± 19 | 43.4 | 502 |
|  | 10 | 130 ± 42 | 44.2 | 427 |
| (7) | 50 | 106 ± 12 | 44.8 | 482 |
|  | 8 | 68 ± 4 | 44.6 | 545 |
| (5) | 40 | 89 ± 4 | 43.8 | 522 |

*Tanaka, A., T. Miyake and T. Mineshita; Acta Endore (Kobenhavn) Suppl. 51, 767, (1960)

Table 9

| Compound administered | Route | LD 50 in mg/Kg (95 % C.L.) |
|---|---|---|
| Ibuprofen | oral | 1350 (1080–1688) |
| FENOPROFEN | oral | 1400 (1129–1736) |
| Compound (5) | | 1120 (875–1434) |
| INDOMETHACIN | oral | 37.5 (27–53) |
| PHENYLBUTAZONE | | 760 (655–882) |
| ASPIRIN | | 1600 (1185–2160) |
| Ibuprofen | oral | 1600 : af 24 H |
| | | 1025 : af 72 H |

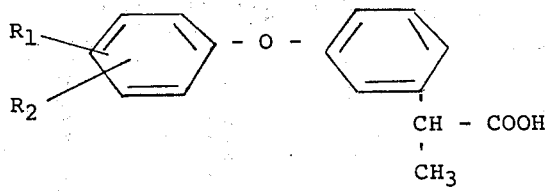

Table 10

Antipyretic activity to the yeast-treated Rats

| Compound administered | Dose mg/kg p.o. | No. of rats | Changes in rectal temperature | | |
|---|---|---|---|---|---|
| | | | 1 hr. | 3 hrs. | 5 hrs. |
| Control | In 5% G.A. | 22 | +0.29 ± 0.05* | +0.20 ± 0.09 | +0.34 ± 0.08 |
| Compound (5) | 1.25 | 4 | +0.25 ± 0.09 | +0.03 ± 0.21 | +0.13 ± 0.15 |
| | 5 | 4 | −0.15 ± 0.13 | −0.30 ± 0.17 | −0.25 ± 0.16 |
| | 20 | 4 | −0.53 ± 0.10 | −0.90 ± 0.10 | −0.70 ± 0.27 |
| | 80 | 4 | −0.55 ± 0.13 | −0.83 ± 0.09 | −0.65 ± 0.16 |
| | 160 | 4 | −0.48 ± 0.14 | −0.90 ± 0.17 | −1.03 ± 0.19 |
| Fenoprofen (1) | 1.25 | 4 | +0.18 ± 0.09 | +0.03 ± 0.22 | +0.05 ± 0.17 |
| | 5 | 4 | −0.33 ± 0.14 | −0.48 ± 0.11 | −0.65 ± 0.19 |
| | 20 | 4 | −0.48 ± 0.22 | −0.85 ± 0.28 | −0.68 ± 0.35 |
| | 80 | 4 | −0.80 ± 0.17 | −1.00 ± 0.04 | −1.15 ± 0.11 |
| | 160 | 4 | −0.50 ± 0.11 | −0.90 ± 0.14 | −0.88 ± 0.12 |
| Ibuprofen | 1.25 | 4 | +0.03 ± 0.05 | +0.05 ± 0.12 | −0.18 ± 0.12 |
| | 5 | 4 | −0.75 ± 0.09 | −0.80 ± 0.21 | −0.20 ± 0.33 |
| | 20 | 4 | −0.65 ± 0.18 | −0.93 ± 0.13 | −0.95 ± 0.15 |
| | 80 | 4 | −0.70 ± 0.25 | −1.03 ± 0.19 | −0.90 ± 0.22 |
| | 160 | 4 | −0.70 ± 0.08 | −0.95 ± 0.28 | −1.03 ± 0.29 |
| Aspirin | 80 | 4 | −0.18 ± 0.10 | −0.25 ± 0.18 | −0.20 ± 0.12 |
| | 160 | 4 | −0.48 ± 0.23 | −1.05 ± 0.18 | −0.95 ± 0.18 |
| | 320 | 4 | −0.75 ± 0.10 | −1.68 ± 0.28 | −1.30 ± 0.29 |

*mean ± S.E.
5% G. A.: 5% gummi arabicum

Table 11

Analgesic activities of test compounds in mice.
Onset time (min.) of writhing syndrome after intraperitoneal injection of 0.7% acetic acid, mean ± S.E.

| Compound administered | Dose mg/kg p.o | Test Compounds alone | Combined with Codeine Phosphate | |
|---|---|---|---|---|
| | | | 10 | 20 |
| Control | 5% G.A. | 4.5 ± 0.4 (72) | 4.8 ± 0.5 (24) | 5.7 ± 0.6 (24) |
| Compound (5) | 10 | 5.2 ± 1.2 (8) | 6.7 ± 1.3 (8) | 6.9 ± 0.7 (8) |
| | 20 | 6.6 ± 1.6 (8) | 6.9 ± 1.3 (8) | 8.6 ± 0.6 (8) |
| | 40 | 5.8 ± 0.4 (8) | 7.1 ± 1.2 (8) | 13.7 ± 1.2 (8) |
| | 80 | 7.8 ± 1.7 (8) | 10.5 ± 1.2 (8) | 14.2 ± 0.8 (8) |
| Fenoprofen | 10 | 3.9 ± 0.3 (8) | 5.3 ± 0.5 (8) | 7.3 ± 1.2 (8) |
| | 20 | 7.1 ± 1.8 (8) | 8.2 ± 1.3 (8) | 7.8 ± 1.2 (8) |
| | 40 | 5.2 ± 1.4 (8) | 10.3 ± 1.5 (8) | 13.8 ± 0.7 (8) |
| | 80 | 8.1 ± 1.7 (8) | 11.8 ± 1.1 (8) | 13.8 ± 0.8 (8) |
| Ibuprofen | 10 | 5.5 ± 1.4 (8) | 4.4 ± 0.3 (8) | 9.2 ± 1.4 (8) |
| | 20 | 5.6 ± 1.4 (8) | 6.0 ± 1.1 (8) | 6.1 ± 0.4 (8) |
| | 40 | 4.5 ± 0.4 (8) | 8.0 ± 1.6 (8) | 11.0 ± 1.4 (8) |
| | 80 | 6.5 ± 1.1 (8) | 9.2 ± 1.3 (8) | 13.3 ± 0.8 (8) |
| Aspirin | 10 | 5.2 ± 1.4 (8) | 5.4 ± 0.4 (8) | 9.6 ± 1.8 (8) |
| | 160 | 5.9 ± 0.8 (8) | 6.2 ± 0.6 (8) | 11.1 ± 1.6 (8) |

Figures in parenthesis indicate numbers of mice

What is claimed is:

1. A 2-(m-phenoxyphenyl)propionic acid derivative represented by the formula:

wherein $R_1$ and $R_2$ are hydrogen or halogen atoms, or trifluoromethyl, lower alkyl or lower alkoxy groups with the proviso that there is no case where both $R_1$ and $R_2$ are simultaneously hydrogen atoms, and pharmacologically acceptable metal salts thereof selected from the group consisting of sodium, potassium, magnesium, calcium and aluminum.

2. A 2-[m-(o-halophenoxy)phenyl]propionic acid represented by the formula:

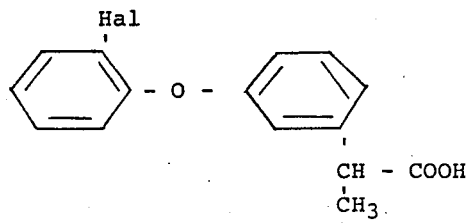

wherein Hal is a halogen atom, and pharmacologically acceptable metal salts thereof selected from the group consisting of sodium, potassium, magnesium, calcium and aluminum.

3. A 2-[m-(p-halophenoxy)phenyl]propionic acid represented by the formula:

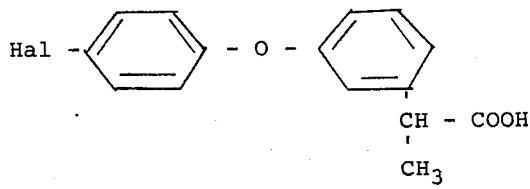

wherein Hal is a halogen atom, and pharmacologically acceptable metal salts thereof selected from the group consisting of sodium, potassium, magnesium, calcium and aluminum.

4. A compound as claimed in claim 1 wherein said compound is 2-[m-(o-chlorophenoxy)phenyl]propionic acid and pharmacologically acceptable metal salts thereof selected from the group consisting of sodium, potassium, magnesium, calcium and aluminum.

5. A compound as claimed in claim 1 wherein said compound is 2-[m-(o-fluorophenoxy)phenyl] propionic acid and pharmacologically acceptable metal salts thereof selected from the group consisting of sodium, potassium, magnesium, calcium and aluminum.

6. A compound as claimed in claim 1 wherein said compound is 2-[m-(p-chlorophenoxy)phenyl] propionic acid and pharmacologically acceptable metal salts thereof selected from the group consisting of sodium, potassium, magnesium, calcium and aluminum.

7. A compound as claimed in claim 1, wherein said compound is the aluminum salt of 2-[m-(o-chlorophenoxy)phenyl] propionic acid, which is produced by adding an aluminum alkoxide to the corresponding acid.

8. A compound as claimed in claim 1, wherein said compound is the aluminum salt of 2-[m-(o-fluorophenoxy)phenyl] propionic acid, which is produced by adding an aluminum alkoxide to the corresponding acid.

9. A compound as claimed in claim 1 wherein said compound is the aluminum salt of 2-[m-(p-chlorophenoxy)phenyl] propionic acid, which is produced by adding an aluminum alkoxide to the corresponding acid.

* * * * *